US 6,936,836 B2

(12) United States Patent
Hösel

(10) Patent No.: US 6,936,836 B2
(45) Date of Patent: Aug. 30, 2005

(54) METHOD AND APPARATUS FOR EXAMINING FIBER MATERIAL TRAVELING IN A FIBER PROCESSING MACHINE

(75) Inventor: Fritz Hösel, Mönchengladbach (DE)

(73) Assignee: Trützschler GmbH & Co. KG, Mönchengladbach (DE)

( * ) Notice: Subject to any disclaimer, the term of this patent is extended or adjusted under 35 U.S.C. 154(b) by 939 days.

(21) Appl. No.: 09/756,683

(22) Filed: Jan. 10, 2001

(65) Prior Publication Data

US 2001/0006220 A1 Jul. 5, 2001

Related U.S. Application Data

(63) Continuation-in-part of application No. 09/658,718, filed on Sep. 11, 2000, now abandoned.

(30) Foreign Application Priority Data

Sep. 9, 1999 (DE) .......................................... 199 43 079

(51) Int. Cl.[7] .............................................. G01N 21/89
(52) U.S. Cl. ............................ 250/559.46; 250/559.41; 250/559.45; 250/559.4
(58) Field of Search ............................. 250/221, 559.4, 250/559.41, 559.46; 382/111; 19/65 A, 150, 239, 297, 300; 209/580, 582, 586, 587, 588

(56) References Cited

U.S. PATENT DOCUMENTS

| 4,953,265 | A | | 9/1990 | Scheinhütte ................. 19/297 |
| 5,544,090 | A | | 8/1996 | Shofner et al. ............... 702/82 |
| 5,642,553 | A | * | 7/1997 | Leifeld .......................... 19/98 |
| 5,752,294 | A | * | 5/1998 | Mor .............................. 19/66 |
| 5,930,870 | A | * | 8/1999 | Leifeld et al. ................ 19/105 |
| 5,974,629 | A | * | 11/1999 | Leifeld et al. ................. 19/98 |
| 6,087,608 | A | * | 7/2000 | Schlichter et al. .......... 209/580 |

FOREIGN PATENT DOCUMENTS

| DE | 41 15 960 | 11/1992 |
| DE | 196 51893 | 6/1998 |
| EP | 0 189 985 | 8/1986 |
| EP | 0 485 881 | 5/1992 |

* cited by examiner

*Primary Examiner*—Allen C. Ho
(74) *Attorney, Agent, or Firm*—Venable LLP; Robert Kinberg; Stuart I. Smith

(57) ABSTRACT

An apparatus for evaluating a fiber web running in a card includes a camera for scanning the fiber web along a length and width portion thereof to detect useful fibers and empty locations in the fiber web and to generate signals representing the useful fibers and empty locations; and an evaluating device connected to the camera for determining a distribution of useful fibers per area unit in the fiber web from the signals.

14 Claims, 5 Drawing Sheets

METHOD AND APPARATUS FOR EXAMINING FIBER MATERIAL TRAVELING IN A FIBER PROCESSING MACHINE

CROSS REFERENCE TO RELATED APPLICATION

This application is a continuation of U.S. application Ser. No. 09/658,718 filed Sep. 11, 2000 now abandoned.

This application claims the priority of German Application No. 199 43 079.9 filed Sep. 9, 1999, which is incorporated herein by reference.

BACKGROUND OF THE INVENTION

This invention relates to a method and an apparatus for examining a fiber web advanced in a fiber processing machine such as a card or a roller card unit. The material of the web is cotton, chemical fibers or the like. The fiber web has useful fibers with intermediate, empty spaces therebetween (hereafter also referred to as empty locations). The apparatus includes a measuring track for the fiber material. The measuring track is associated with a camera, such as a diode matrix camera which is connected with an evaluating device such as an image processing computer.

German Offenlegungsschrift (application published without examination) 39 28 279 to which corresponds U.S. Pat. No. 5,130,559, describes an apparatus in which foreign particles are recognized in the fiber flow in order to determine the degree of soiling (trash content) of the fiber material by optical and electronic means. For this purpose a sensor detects each foreign individual particle in the running fiber web and, by means of an evaluating device, for each individual particle specific characterizing magnitudes are determined (particularly gray scale and edge detection) to identify the matter as a foreign particle. In this manner, the foreign particles are differentiated from the useful fibers. The foreign particles form locally sharply delimited defective locations which are concentrated in a very small space. Further, such foreign particles display a different behavior with respect to the useful fibers; for example, neps (fiber knots which have a diameter less than 1 mm) appear as dots of increased reflection and may therefore be separated from the other signals. The individual particles are determined as differing from the remaining fiber web which only represents a background. The smaller the selection of the scanned surface region of the fiber web, the more conspicuous the appearance of a nep.

It is a disadvantage of the above-outlined conventional arrangement that a detection and determination of the degree of homogeneity of the fiber web is not feasible. Also, such conventional arrangement is not concerned with a determination of the distribution and orientation of the useful fibers.

SUMMARY OF THE INVENTION

It is an object of the invention to provide an improved method an apparatus of the above-outlined type which eliminates the discussed disadvantages and which, in particular, improves a detection and determination of the homogeneity of the fiber web, particularly the distribution and orientation of useful fibers and furthermore improves the degree of fiber web uniformity.

This object and others to become apparent as the specification progresses, are accomplished by the invention, according to which, briefly stated, the apparatus for evaluating a fiber web running in a card includes a camera for scanning the fiber web along a length and width portion thereof to detect useful fibers and empty locations in the fiber web and to generate signals representing the useful fibers and empty locations; and an evaluating device connected to the camera for determining a distribution of useful fibers per area unit in the fiber web from the signals.

According to the invention, the useful fibers and voids, that is, the spaces (empty locations) between the useful fibers are detected and evaluated. From the ratio between the useful fibers and the empty locations per area unit the homogeneity and the web irregularity (cloudiness) is determined, whereby the distribution and orientation of the useful fibers in the fiber web are ascertained. The measuring values permit an image display and an optical and electronic evaluation. By examining the homogeneity, defects in the region of the roll clothings or an incorrect fiber feed may be detected and thus the quality of the produced fiber web may be improved. The homogeneity of the web produced by the carding machine or the roller card unit is automatically and continuously detected and evaluated so that by means of the machine control and setting members the processing of the fiber material may be affected. The greater the selected scanned surface area, the better the detectability of the distribution of the useful fibers.

The invention has the following additional advantageous features:

Determining the numerical distribution of the useful fibers;

Determining the spatial distribution of the useful fibers;

Detecting impurities, such as neps and distinguishing such impurities from the useful fibers;

Disregarding impurities, such as neps, when determining the distribution of useful fibers;

Determining the area share of useful fibers and empty locations per unit area;

Determining the distribution of dense and thin areas of useful fibers per unit area and comparing such distributions with stored comparison values for the fiber web;

Determining the distribution of dense and thin areas of useful fibers per unit area and comparing such distributions with a homogeneous fiber web; and Utilizing a digital image data processing in the evaluating device.

DESCRIPTION OF THE PREFERRED EMBODIMENTS

Figure 1:
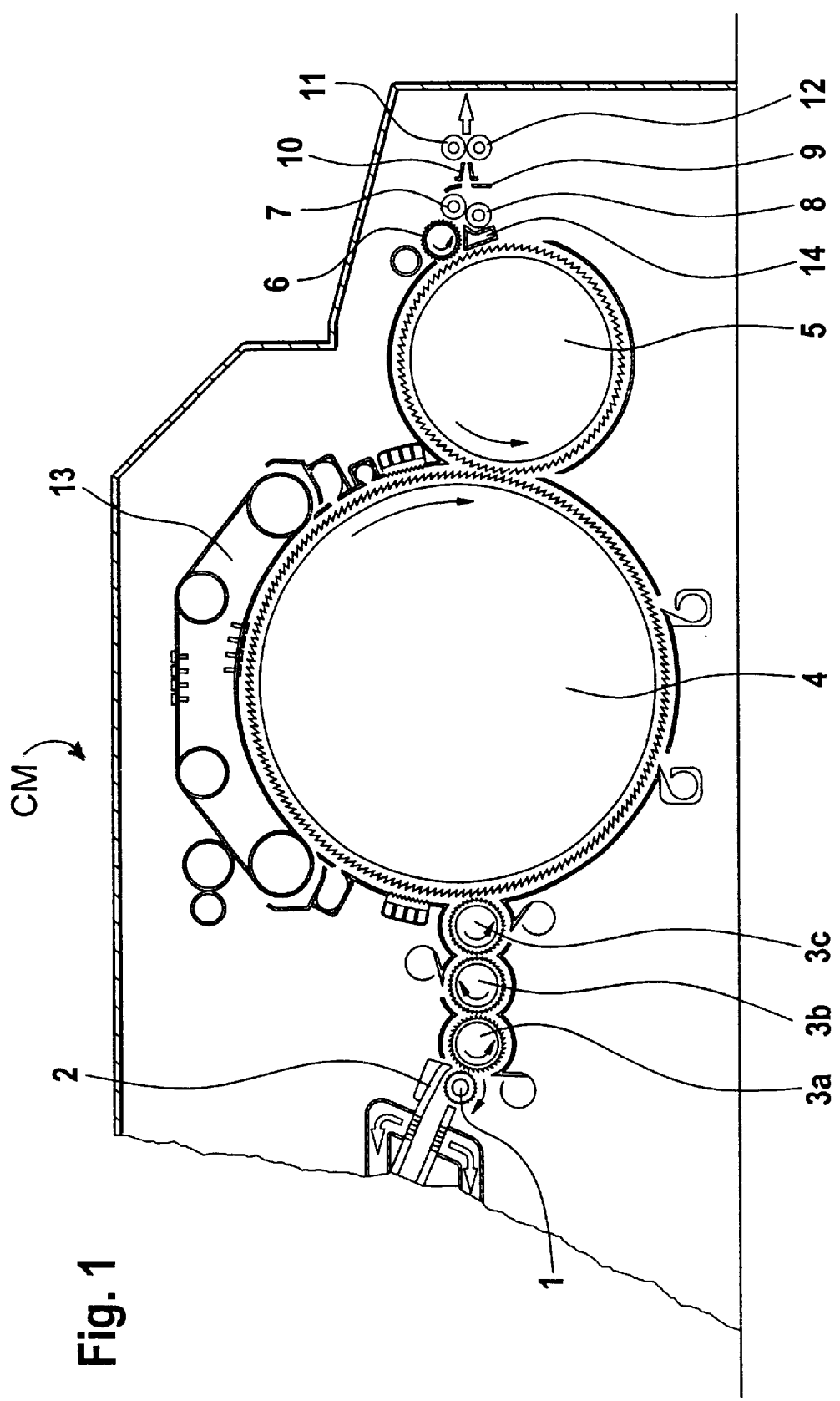
FIG. 1 is a schematic side elevational view of a carding machine including a web supporting and guiding body housing a camera and an illuminating assembly for practicing the method according to the invention.

FIG. 1 illustrates a high performance carding machine CM which may be, for example, a DK 903 model manufactured by Trützschler GmbH & Co. KG, Mönchengladbach, Germany.

The carding machine CM has a feed roll 1, a feed table 2 cooperating with the feed roll, licker-ins 3a, 3b and 3c, a main carding cylinder 4, a doffer 5, a stripping roll 6, cooperating crushing rolls 7 and 8, a web guiding element 9, a web trumpet 10, cooperating pull-off rolls 11 and 12 and a traveling flats assembly 13. Underneath the stripping roll 6 a web supporting and guiding body 14 is provided. The upper crushing roll 7 is in a close proximity to the stripping roll 6. The direction of rotation of the main carding cylinder 4 and the rolls are shown by the curved arrows drawn thereinto.

Figure 2:
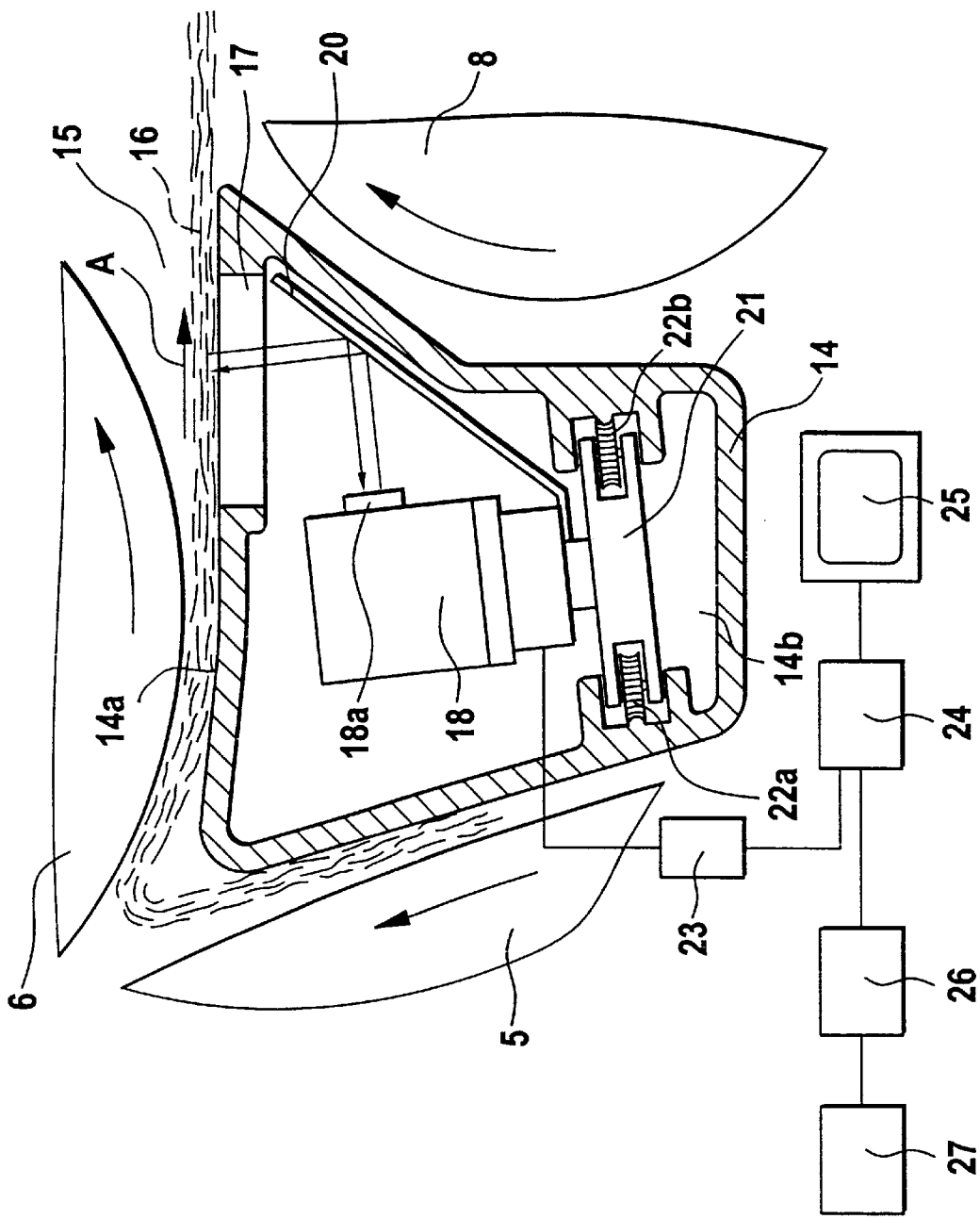
FIG. 2 is a schematic sectional side elevational view of the apparatus for practicing the method according to the invention, including a block diagram.

Turning to FIG. 2, in the region 15 of the carding machine the fiber web 16 leaves the stripping roll 6 and advances, as indicated by the arrow A, toward the crushing rolls 7, 8 on the surface 14a of the supporting and guiding body 14 which has a generally rectangular cross-sectional outline. The web supporting surface 14a is slightly concave and has a radius of curvature which is greater than the radius of the stripping roll 6.

The supporting and guiding body 14 is configured as a housing, and its upper wall, which includes the web supporting surface 14a, is provided with a transparent window 17. The fiber web as it progresses from the main carding cylinder 4, is first positioned on the clothing of the doffer 5 and then taken over by the clothing 6a of the stripping roll 6. Slightly beyond a vertical center plane of the stripping roll 6, oriented perpendicularly to the advancing direction A, the web 16 leaves the stripping roll 6 and, guided over the window 17, enters the nip between the crushing rolls 7, 8 and passes therethrough. At the supporting surface 14a, one end of the body 14 extends into the gap zone between the doffer 5 and the stripping roll 6, while its other end projects into the gap zone between the stripping roll 6 and the crushing rolls 7, 8.

Figure 2A:
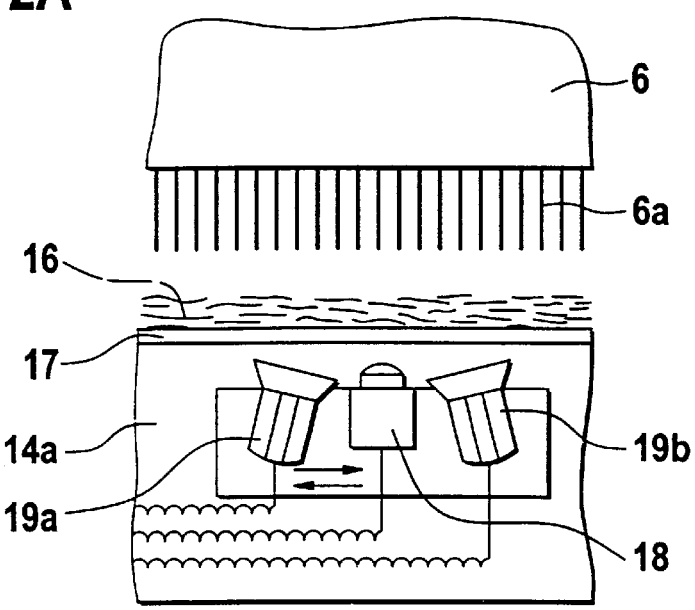
FIG. 2a is a schematic top plan view of a back-and-forth travelling carriage on which the camera and the illuminating assembly are mounted.

The body 14 is an extruded hollow member made, for example, of aluminum and also functions as a housing. Also referring to FIG. 2a, a camera 18, such as a diode matrix camera, an illuminating assembly composed of illuminating devices 19a, 19b and a mirror 20 are mounted on a carriage 21 disposed in the inner space 14b of the body 14. The camera 18 may be a diode line camera, it may have an optical component and an electronic component with a CCD chip. The reflecting mirror 20 is positioned at an angle between an objective 18a of the camera 18 and the illuminating assembly, on the one hand, and the inner face of the window 17, on the other hand. The carriage 21 runs, on wheels 22a, 22b engaging rails on the inner wall of the body 14, perpendicularly to the drawing plane of FIG. 2, along the width of the carding machine, that is, transversely to the advancing direction A. Such a web supporting and guiding body, accommodating an equipment for taking pictures of a running fiber web in a carding machine is generally also disclosed in U.S. Pat. No. 5,692,267.

Figure 5:
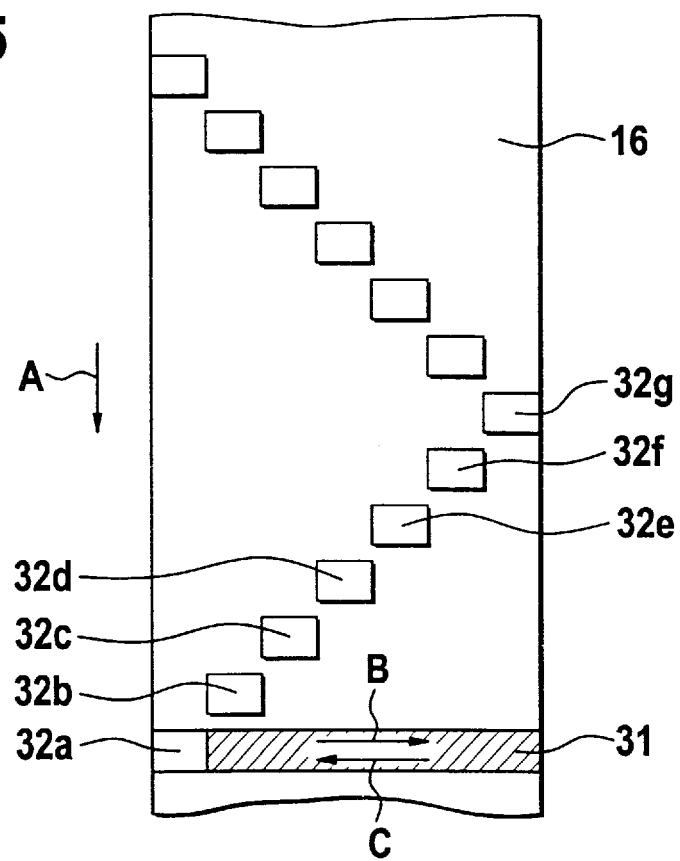
FIG. 5 is a schematic to plan view of the fiber web indicating captured regions in the longitudinal and transverse direction.

As the camera 18 reciprocates along the width of the carding machine, it delivers sharp images of the fiber web 16 even in case of a card output of 300 m/min and transmits the image signals to an image processing computer 23 such as a microcomputer with microprocessor. The latter evaluates the images 32a–32g as shown in FIG. 5, based on the distribution of the useful fibers in the web 16 per surface unit. The results are shown in a display 25 via a machine control 24 which may be, for example, a Card-Commander model manufactured by Trützschler GmbH & Co. KG. Additionally or as an alternative, the image signals are for further processing transmitted to an information system 28 which may be a KIT model manufactured by Trützschler GmbH & Co. KG. The machine control 24 is followed by a control element 26 and a setting device 27 for affecting the distribution of the useful fibers in the fiber web 16. The setting device 27 may trigger measures for changing the fiber distribution in the web 16, for example, it may effect a change in the distance between the flat clothings and the cylinder clothing of the card, or the rpm of the cylinder or the distance between a guide element of a roll or may initiate a sharpening of the roll clothings.

The apparatus according to the invention may be installed in, and removed from, a carding machine in a simple manner and thus a periodic measurement on different cards with the same apparatus may be carried out.

As the fiber web 16 passes over the window 17, the camera 18 takes pictures under reflected flash light illumination, as shown in FIG. 2. The evaluation is effected in principle as a desired value/actual value comparison. The reflection intensity related to the incident ray intensity is utilized as a desired parameter. A reflected light producing module includes a semiconductor flash device with high homogeneity and the command-controlled high speed measuring camera 18. The camera 18 may have a digital data output as described, for example, in German Offenlegungsschrift No. 43 13 621. In case a transmitted light assembly is used, the latter includes a large-surface semiconductor flash device of high intensity.

During operation, light flashes are produced as controlled by the camera 18 or the camera control. For the individual exposures light of different wavelengths may be used. Also, more than one illuminating device may be used for each exposure. For example, a reflected light assembly may use more than one illuminating device. The illumination may occur from different directions. Further, illumination may be effected from different sides (transillumination and reflection). For the illumination light sources with different wavelengths may be used. Further, various exposure times (flash duration) may be set.

By means of the apparatus according to the invention an automatic detection and reduction of the irregularities of the fiber web 16 may be effected. It is of importance to detect the fiber web as it advances freely after its removal from the stripping roll 6. While the invention has been described in connection with a carding machine, it will be understood that it may find application in other machines in which a fiber web is produced, such as a roller card unit.

Figure 3:
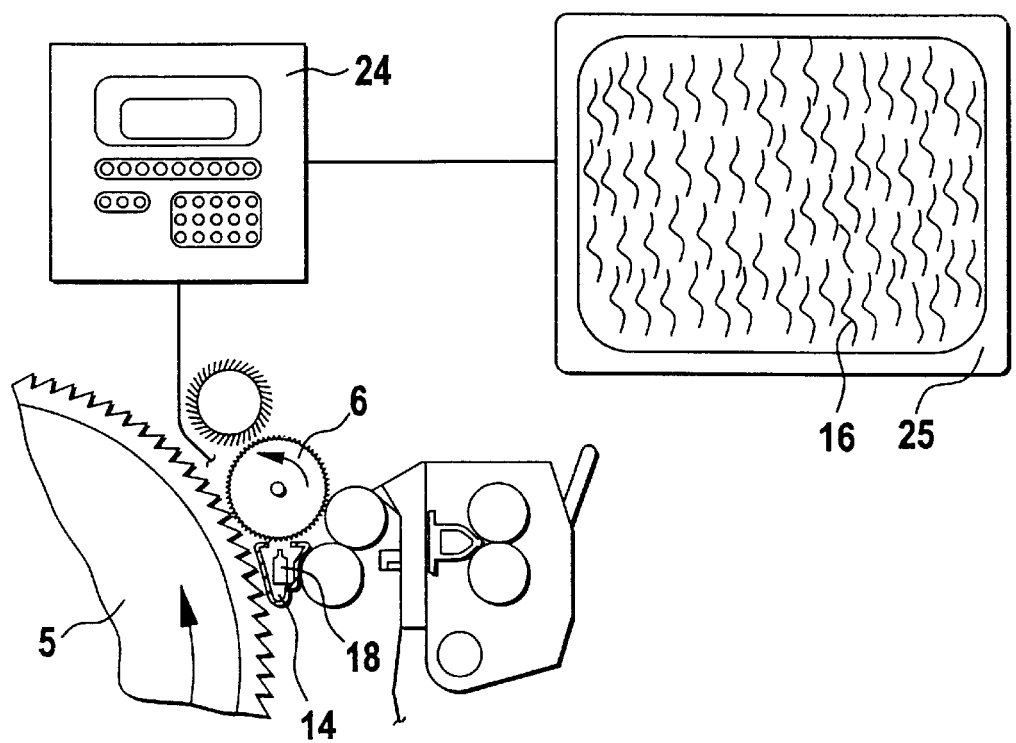
FIG. 3 is a fragmentary schematic sectional view of the carding machine and also showing a computer and a display device illustrating a distribution of usable fibers and spaces therebetween.

FIG. 3 shows an image screen 25 on which the fiber web 16 is reproduced, illustrating useful fibers and intermediate spaces therebetween. The homogeneity (cloudiness), that is, the distribution and orientation of the useful fibers is represented. The objective 18a of the camera 18 is, according to FIG. 3, oriented upwardly toward the fiber web 16 without a deflecting mirror as opposed to the arrangement according to FIG. 2a.

Figure 4:
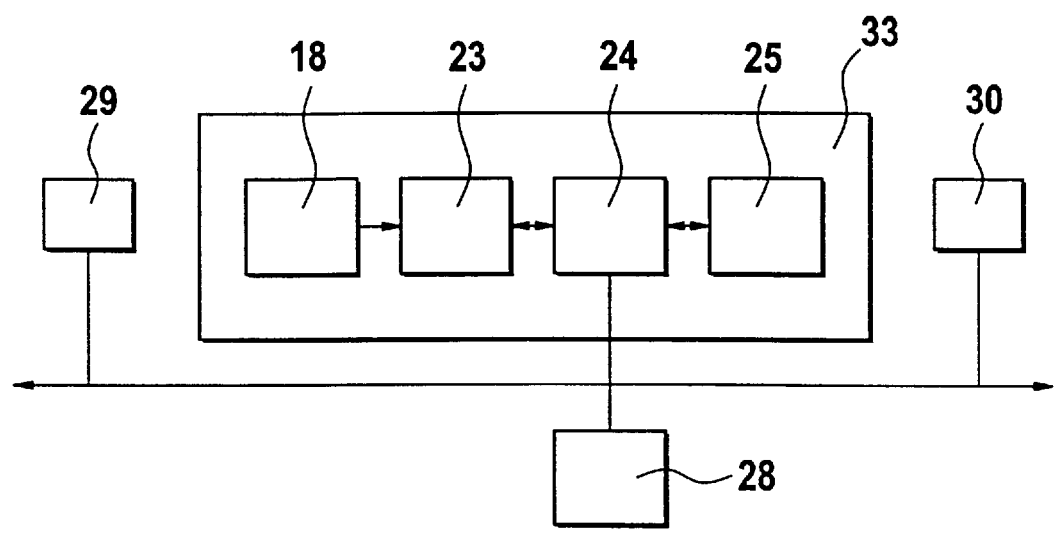
FIG. 4 is a block diagram of the apparatus according to the invention.

The block diagram of FIG. 4 shows the camera 18 followed by the image processing computer 23, the card control device 24 and the display device 25. When the obtained information data are, for example, transmitted to the card control 24 and therefrom to other superordinated monitoring systems such as the device 28, a comparative monitoring of several machines is feasible and also, comparisons with earlier results may be made.

As shown in FIG. 5, the camera 18 continuously delivers samples in the longitudinal and transverse direction of the web 16. The evaluation of the images is effected according to the methods of digital image processing. Statistically supported determinations, for example, concerning the quality of the web (homogeneity) is feasible by applying suitable mathematical methods.

The shaded area 31 indicates the scanning surface of the camera 18, moved parallel to the width of the machine, in the direction of the arrows B and C. The sample images taken are designated at 32a–32g.

Figure 6A:
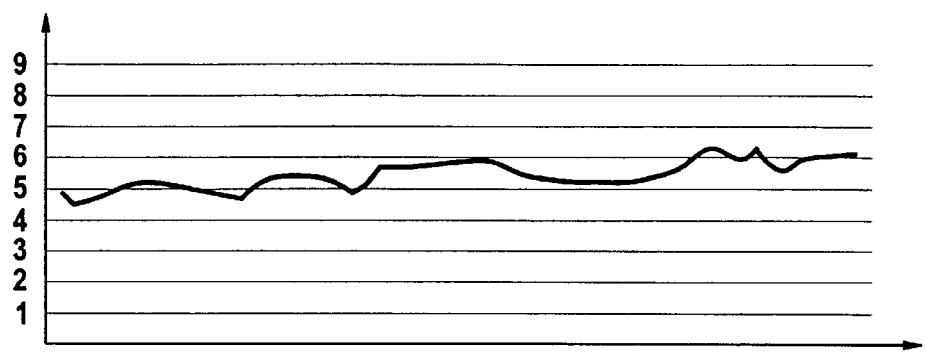
FIG. 6a is a diagram showing the homogeneity of the fiber web as a function of time (longitudinal direction for a defined track).
Figure 6B:
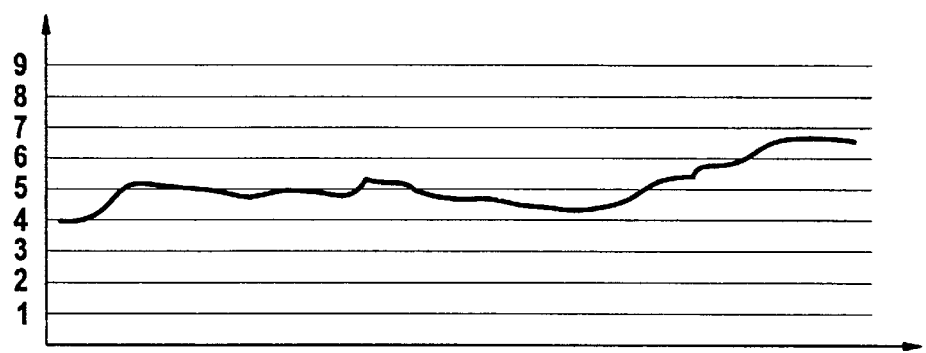
FIG. 6b is a diagram showing the homogeneity of the fiber web as a function of time (in a transverse direction and illustrating a mean value for all tracks).
Figure 6C:
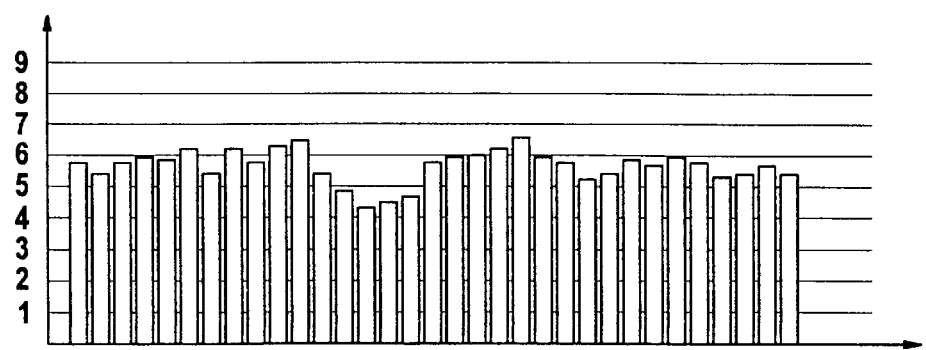
FIG. 6c is a bar diagram illustrating the homogeneity of the fiber web (width distribution).

Based on known fiber web structures a normalization factor may be determined so that both for the length and for the width of the fiber web 16 time-dependent quality data may be obtained. For example, a highly satisfactory fiber web may be designated with the factor 10 and a very inferior quality may be assigned the factor 0. In this manner, respective assertions may be made (FIGS. 6a–6c). A similar process may be performed for the width distribution.

It will be understood that the above description of the present invention is susceptible to various modifications, changes and adaptations, and the same are intended to be comprehended within the meaning and range of equivalents of the appended claims.

What is claimed is:

1. An apparatus for evaluating a fiber web running in a card, comprising:
   (a) a camera for scanning the fiber web along a length and width portion thereof to detect useful fibers and empty locations in the fiber web and to generate signals representing the useful fibers and empty locations; and
   (b) evaluating means connected to said camera for determining a distribution of useful fibers per area unit in the fiber web from the signals.

2. A method of evaluating a fiber web running in a card, comprising the following steps:
   (a) scanning with a camera the fiber web along a length and width portion thereof;
   (b) detecting useful fibers and empty locations in the fiber web by the camera;
   (c) generating signals representing the useful fibers and empty locations;
   (d) applying the signals to an evaluating device connected to the camera; and
   (e) determining, by the evaluating device, a distribution of useful fibers per area unit in the fiber web from the signals.

3. The method as defined in claim 2, further comprising the step of determining a numerical distribution of the useful fibers.

4. The method as defined in claim 2, further comprising the step of determining a spatial distribution of the useful fibers.

5. The method as defined in claim 2, further comprising the step of detecting impurities.

6. The method as defined in claim 5, further comprising the step of distinguishing the impurities from the useful fibers.

7. The method as defined in claim 2, further comprising the step of determining an area share of useful fibers and empty locations per unit area.

8. The method as defined in claim 2, further comprising the step of determining a distribution of dense and thin areas of useful fibers per unit area.

9. The method as defined in claim 8, further comprising the step of comparing said distribution with stored comparison values for the fiber web.

10. The method as defined in claim 8, further comprising the step of comparing said distribution with a homogeneous fiber web.

11. The method as defined in claim 2, further comprising the step of utilizing a digital image data processing in the evaluating device.

12. The method as defined in claim 2, further comprising the step of stepwise detecting the useful fibers and empty locations by the camera.

13. The method as defined in claim 2, further comprising the step of scanning the fiber web at random.

14. The method as defined in claim 2, further comprising the step of statistically evaluating the measuring signals.

* * * * *

UNITED STATES PATENT AND TRADEMARK OFFICE
CERTIFICATE OF CORRECTION

PATENT NO. : 6,936,836 B2
DATED : August 30, 2005
INVENTOR(S) : Fritz Hosel

It is certified that error appears in the above-identified patent and that said Letters Patent is hereby corrected as shown below:

<u>Title page,</u>
Item [*] Notice, the Term Patent Adjustment should be -- (708) days --.

Signed and Sealed this

Sixth Day of June, 2006

JON W. DUDAS
*Director of the United States Patent and Trademark Office*